(12) United States Patent
Thilly et al.

(10) Patent No.: US 7,365,343 B2
(45) Date of Patent: Apr. 29, 2008

(54) APPARATUS AND PROCESS FOR FILLING A MEDICAMENT INTO A CONTAINER

(75) Inventors: Jacques Thilly, Rixensart (BE); Christian Vandecasserie, Rixensart (BE)

(73) Assignee: GlaxoSmithKline Biologicals s.a., Rixensart (BE)

( * ) Notice: Subject to any disclaimer, the term of this patent is extended or adjusted under 35 U.S.C. 154(b) by 267 days.

(21) Appl. No.: 10/546,682

(22) PCT Filed: Feb. 19, 2004

(86) PCT No.: PCT/EP2004/001752

§ 371 (c)(1),
(2), (4) Date: Jan. 11, 2006

(87) PCT Pub. No.: WO2004/076288

PCT Pub. Date: Sep. 10, 2004

(65) Prior Publication Data

US 2006/0151714 A1    Jul. 13, 2006

(30) Foreign Application Priority Data

Feb. 25, 2003    (GB) .................................. 0304386.6

(51) Int. Cl.
*B65B 55/08*    (2006.01)
*B65B 31/02*    (2006.01)
*A61L 2/08*    (2006.01)

(52) U.S. Cl. .............................. 250/455.11; 250/492.3; 53/425; 141/2; 141/11; 141/85; 141/130; 141/329; 141/330

(58) Field of Classification Search ............. 250/492.3, 250/453.11, 454.11, 455.11; 53/425; 141/2, 141/11, 85, 130, 329, 330
See application file for complete search history.

(56) References Cited

U.S. PATENT DOCUMENTS

| 3,780,308 A | * | 12/1973 | Nablo ..................... 250/492.3 |
| 4,652,763 A | | 3/1987 | Nablo |
| 5,129,212 A | * | 7/1992 | Duffey et al. ................. 53/426 |
| 5,641,004 A | | 6/1997 | Py |
| 5,925,885 A | | 7/1999 | Clark et al. |
| 6,285,030 B1 | * | 9/2001 | Williams et al. ....... 250/454.11 |
| 6,929,040 B2 | * | 8/2005 | Py ............................. 141/329 |
| 2002/0172615 A1 | | 11/2002 | Woodworth et al. |

FOREIGN PATENT DOCUMENTS

WO      WO02/064439      8/2002

* cited by examiner

*Primary Examiner*—Jack I. Berman
(74) *Attorney, Agent, or Firm*—Jeffrey A. Sutton; Charles M. Kinzig

(57) ABSTRACT

Apparatus for introducing a medicament into containers, especially vials, in which the containers are passed through an enclosure and exposed therein to a sterilising electron beam. The containers are then conveyed to a filling station situated outside the enclosure at which a wall part of the container is punctured with a filling needle and medicament introduced into the container via the needle then withdrawing the needle. Preferred apparatus also includes means for heat sealing the puncture site. A corresponding process is disclosed.

25 Claims, 3 Drawing Sheets

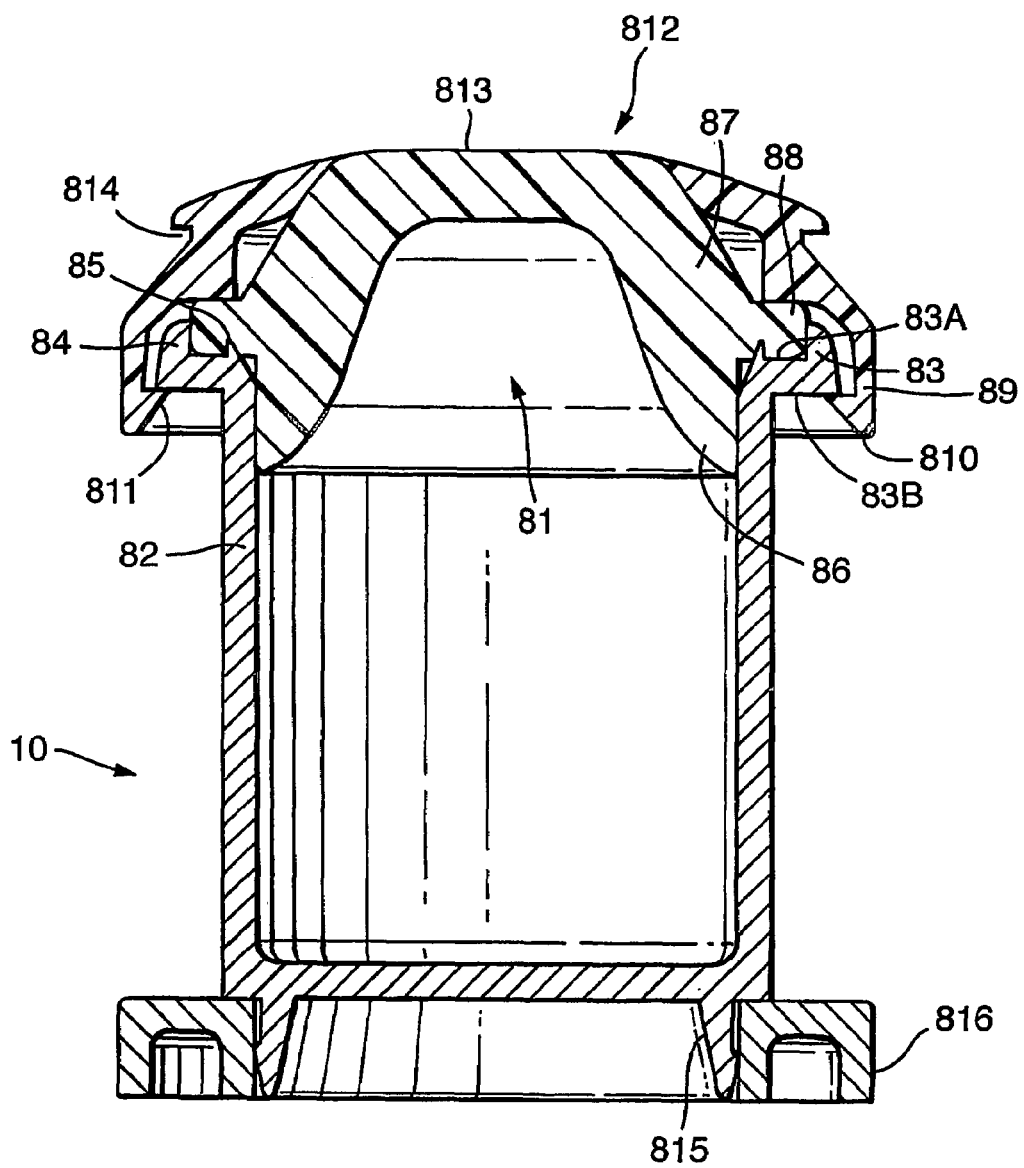

APPARATUS AND PROCESS FOR FILLING A MEDICAMENT INTO A CONTAINER

This invention relates to a novel apparatus for filling sterile containers, particularly pharmaceutical vials, with medicament, and more specifically to a part of such an apparatus in which the outside of containers to be filled are sterilised. The invention also relates to a novel process performed by this apparatus.

A process is known from U.S. Pat. No. 5,641,004, US-A-2002/0023409 and WO-A-02/064439 in which a medicament is sealed into a container, particularly a vial having a puncturable and fusible closure, by sterilising the interior of the container e.g. by gamma ray sterilisation, then at a filling station puncturing the closure with a hollow filling needle, introducing the medicament into the interior of the vial through the needle, withdrawing the needle, then sealing the puncture site by directing a laser beam onto the site to fuse the material adjacent to the puncture site, then allowing the material to cool and re-solidify.

Processes and equipment for performing this process have not been optimised, particularly in satisfactorily meeting the requirement of sterilising the outside of the container, especially in the region of the puncture, and interfacing sterilising equipment with the filling station.

WO-A-04/000100 (published only after the present priority date) discloses a sterile filling machine in which an e-beam is used to sterilise the outside of vials. In the machine disclosed therein the filling member, e.g. the needles used to inject medicament into the vials, is mounted within the same chamber as the e-beam. This leads to a cumbersome construction of machine because the e-beam chamber must be shielded to prevent the X-rays resulting from the e-beam from escaping from the chamber. If the filling member is within the e-beam chamber a large quantity of heavy shielding is required. Also corrosive ozone produced by the e-beam can come into contact with the filling means.

It is an object of this invention to provide an improved process of this type, and improved apparatus for performing this process.

According to a first aspect of this invention there is provided an apparatus for introducing a medicament into a container, comprising:

an enclosure which encloses means for exposing a wall part of the container to a beam of electrons of a sufficient energy and dose to inactivate microorganisms present on the wall part of the container, means to transport a container into said enclosure, means to transport the container out of said enclosure, a filling station being situated outside of the enclosure and comprising means for puncturing the container with a filling needle, introducing the medicament into the container via the needle then withdrawing the needle, means for transporting a container which has been exposed to said beam of electrons from the enclosure to the filing station, means for providing a sterile environment around the container whilst the container is transported from the enclosure to the filling station.

Preferably the apparatus also comprises a sealing station at which the residual puncture site is sealed by melting the material adjacent to the puncture site and then allowing the material to solidify.

According to a second aspect of this invention a process for introducing a medicament into a container is provided, comprising the steps:

(1) providing a container having a wall part of a material which can be punctured by a filling needle and thermoplastically melted, (2) introducing the container into an enclosure which encloses a means for exposing the wall part of the container to a beam of electrons of a sufficient energy and dose to inactivate microorganisms present on the wall part of the container, (3) exposing the wall part to a beam of electrons of a sufficient energy and dose to inactivate microorganisms present on the wall part, whilst the container is in said enclosure, (4) transporting exposed containers from (3) out of the enclosure, and transporting them in a sterile environment to a filling station, (5) at the filling station puncturing the wall part with a filling needle, introducing the medicament into the container via the needle, and withdrawing the needle.

Preferably step (5) is followed by a step (6) transporting filled containers from step (5) to a sealing station where the residual puncture site is sealed by melting the material adjacent to the puncture site and then allowing the material to re-solidify.

The term "sterile" herein in relation to atmospheres such as air relates to any atmosphere which has been filtered or otherwise treated to remove micro-organisms, for example HEPA filtered air. The sterility of such air is normally expressed in terms of a class number, for example class 100 or better. Within such a sterile environment pieces of equipment e.g. parts of machinery may be sterilised to remove microorganism activity, e.g. using steam, heat or radiation sterilisation.

Containers suitable for step (1) are known, e.g. vials having a body made for example of glass or a plastics material, with a wall part being a closure made from an elastomeric polymer which can be punctured with a filling needle and melted by for example directing a laser beam at the puncture site. A suitable type of plastics material is a cyclo-olefin copolymer ("COC"), a blend thereof or a blend thereof with another polymer. Examples of such COC polymers are for example disclosed in U.S. Pat. No. 5,723,189, EP-A-0436372 and EP-A-0556034 among others. A suitable hard plastic material accepted for use in the pharmaceutical industry is the cyclo-olefin copolymer "Topas™" made by Celanese Corporation or Zeonex™ made by Zeon Corporation. For example the known COC polymers Topas 8007 or Topas 6015 may be used, available from for example Ticona GmbH (DE). Conditions for injection moulding this polymer to make vials therefrom are known in the art.

The closure part of the container may for example be a thermoplastic elastomer ("TPE") such as a styrene-butadiene-styrene or "SEBS" block copolymer, for example a blend of the polymers "Engage" supplied by Dupont-Dow, and "Dynaflex" formerly known as "Kraton" as supplied by Shell but now available from GLS (USA) who supply this blend, and including a dye, e.g. grey, to enhance absorption of laser light so that the elastomer material may be heated using laser light. Under irradiation from a focused 980 nm laser of power ca. 6-10 w this polymer easily fuses at ca. 180° C. and sets on cooling. A particular type of such a vial is disclosed in applicant's co-pending PCT/EP03/09151 filed 15 Aug. 2003, incorporated herein by reference, and in the art cited above.

The vial of PCT/EP03/09151 is briefly described below. This vial has a mouth opening and a neck immediately downward of the mouth opening, and has a rim in the form of a flange having upper and lower surfaces extending transverse to the upper-lower axis, and as provided for the process of the present invention is provided with a closure system comprising:

an elastomer closure part shaped to sealingly engage with the mouth opening, having a lower surface facing the interior of the vial and an opposite upper surface facing away from the vial, and capable of being punctured by a needle, and a clamp part able to engage with the vial, particularly with the rim of the mouth opening, and able to bear upon the upper surface of the closure part to hold the closure part in a closing relationship with the mouth opening, the clamp part having an aperture therein through which a region of the upper surface of the closure part is exposed when the clamp part is engaged with the vial.

Suitably the filling needle in step (5) may be inserted through the part of the closure exposed through the aperture.

The terms "upward", "upper", "lower" etc. and derived directional terms such as "vertical" are based on the normal configuration of a vial in a vertical orientation with the mouth uppermost and its base downward.

Apparatus and methods for performing step (5) and the optional but preferred step (6) are also known, for example as disclosed in the art cited above, in particular U.S. Pat. No. 5,641,004 and WO-A-02/064439.

The containers e.g. vials are preferably transported into respective stations at which steps (3), (5) and (6) may be performed by a generally conventional conveyor system. Preferably in such a conveyor system containers such as vials are mounted having their mouth and closure uppermost, so that the part of the container, e.g. the closure of a vial, which is exposed to the electron beam in step (3) and punctured in step (5) is distant from the conveyor. This facilitates the creation of a sterile environment by means of a downward flow, e.g. a laminar flow, of sterilised air e.g. of class 100 or better, so that the bulk of the container e.g. the vial, and the conveyor are downstream of the part of the container which is exposed to the electron beam.

In a preferred form of the apparatus and process, step (3) is performed within an enclosure comprising part of the apparatus and which is bounded by a surrounding wall, having an entrance opening via which a container may enter the enclosure, and an exit opening via which a container may exit the enclosure, and within which is located a source of a beam of electrons. This enclosure is preferably a shielded enclosure such that electron beam radiation and X-ray radiation caused by the electron beam cannot escape from the enclosure at an intensity likely to cause damage or injury. Suitable forms of shielding are known in the art, e.g. metal screens, especially lead blocks.

Suitably plural containers such as vials are introduced into the enclosure serially in line with the conveying direction, by means of a conveyor which enters the enclosure through the entrance opening and leaves via the exit opening, e.g. on one or more conveyor that conveys plural vials in one or more serial lines. Plural vials may in this way be exposed to the electron beam, then be transported out of the enclosure and toward the filling station. Such a conveyor may be of a generally conventional construction. Suitably the conveyor may follow a convoluted path within the enclosure, e.g. bending within the enclosure shortly after entering via the entrance opening and shortly before reaching the exit opening. By such a convoluted construction a straight line path from the electron beam source to the entrance and/or exit openings can be avoided so as to reduce the possibility of escape of radiation. Additionally or alternatively the conveyor may bend shortly outside the entrance and/or the exit opening, so that shielding can be placed in any straight line path extrapolated from the electron beam source and through either or both of these openings.

In step (4) transporting exposed containers from (3) in a sterile environment to a filling station, the enclosure in which the containers e.g. vials are exposed to the electron beam is distanced from the filling station of step (5), for example in the apparatus being separated therefrom by a length of conveyor system.

It is preferred that in the apparatus and process, after step (3) the containers, e.g. vials, having been exposed to the electron beam are transported into an area in which a purified downward laminar flow of air is maintained within vertical barriers which isolate at least the filling station and the optional sealing station from the ambient environment, and are maintained in such an environment during filling step (5) and sealing step (6), and until these steps are completed.

It is preferred that between the enclosure in which step (3) is performed, and the filling station of step (5) the container, e.g. vial is passed through a region downstream of step (3) of pressurised sterile atmosphere, e.g. of pressurised sterile air, e.g. class 100 or better, which is in communion with the interior of the enclosure. For example such a region may be downstream adjacent to the exit opening of the enclosure. The effect of such a region can be to direct a flow of sterile atmosphere in a direction opposite to, i.e. upstream of, the conveying direction. This can reduce the possibility of contamination being carried downstream into the areas where steps (5) and optionally (6) are performed, where environmental sterility can be important. This flow can also help to flush ozone out of the enclosure.

The apparatus may incorporate means for providing such a region. Such means may comprise a compartment located downstream in the conveying direction from the enclosure, provided with a means to introduce the pressurised atmosphere into the compartment, such as an inlet conduit, having an entrance for the container, the entrance being in communion with the exit opening of the enclosure, and having an exit for the container. The conveyor may pass through the compartment from the entrance to the exit. The entrance of this compartment may be larger than the exit so that the pressurised atmosphere preferentially leaves the compartment via the entrance. A suitable pressure for the pressurised atmosphere is 20-70 Pascals, e.g 50-60 Pascals.

The sterile environment through which the containers are transported in step (4), and in which step (5) and optional step (6) is performed, is preferably provided by a flow, preferably downward, of sterile air, preferably of Class 100 or better, and means are known for providing such a flow in the apparatus e.g. a HEPA filter. With a conveyor system on which containers such as vials are held on the conveyor adjacent to their base, with the vials having their mouth and closure uppermost such an arrangement allows a downward flow of purified air to be directed over the containers, with the part that is exposed to the electron beam and punctured being at an upstream location in the air flow relative to the conveyor. This ensures that any areas of the container which have not been exposed to the electron beam are upstream in the flow of air and contamination cannot be carried by the air flow toward the exposed wall part at which the puncture is made.

After being exposed to the electron beam in step (3), containers e.g. plural vials are transported in step (4) to the filling station. In the filling station used in step (5) the vials are transported to a position adjacent to a filling apparatus, which is preferably configured so that the filling apparatus can operate to fill plural vials simultaneously. Numerous types of filling apparatus suitable for simultaneously filling plural vials moving on a conveyor are known.

It is preferred that at the filling station plural vials for filling are arranged in rows of plural vials in an alignment across the direction of the conveyor. Therefore in the process and apparatus, in transporting step (4), if in step (3) plural vials are being conveyed in a serial line in line with the conveying direction, to achieve this alignment it is necessary to convert such serial movement of plural vials in line with the conveying direction into movement in the conveying direction of rows of plural vials aligned across the conveying direction. Correspondingly in the apparatus it would in such a case be necessary to provide means between the enclosure used in step (3) and the filling station of step (5) to convert such serial movement of plural vials in line with the conveying direction into movement in the conveying direction of rows of plural vials aligned across the conveying direction.

Therefore between process step (3) and step (5), e.g. in step (4) it is preferred to transfer vials from a first conveyor on which they are transported through the enclosure in which step (3) is performed in a serial line aligned with the conveying direction onto a subsequent conveyor on which the plural vials are aligned in plural rows across the conveying direction, and in the apparatus to provide means for doing this. Numerous types of machinery for achieving this are known in the conveying art, such as the so called "floating pulley" conveyor system. For example it may be preferable to transfer the containers from the first conveyor to the subsequent conveyor, via an intermediate conveyor.

Filling step (5) and sealing step (6) are suitably performed within a sterile environment, typically provided by a downward flow of sterile air maintained within an area bounded by a vertically extending barrier within which is the filling station and sealing station. The abovementioned compartment may have its exit opening in communication with an opening through such a barrier and through which opening the conveyor may pass.

When step (5) is performed it is preferred that the container is held against the force of the needle being withdrawn, e.g. if the needle is withdrawn upwards the container should be held down. By holding the container in this way the container may be prevented from being pulled off the conveyor when the needle is withdrawn. Means in the apparatus for doing this may be provided. For example vials may be held in a stand with an upward facing surface against which a holder may bear. Such stands are disclosed in PCT/EP03/09151, and suitable holding means for such vials in such stands is disclosed in PCT/EP03/10349. The filling station and/or sealing station of respective steps (5) and (6) may comprise respectively filling needles and means to direct laser light enclosed in respective aerodynamic shrouds, which can minimise disruption to the sterile airflow over the filling station and/or sealing station. Such a filling station and/or sealing station enclosed in respective aerodynamic shrouds are disclosed in PCT/EP03/10349.

Following sealing step (6) the container, e.g. a vial, may be subjected to further processing, e.g. capping, secondary packaging etc. When the container is a vial as disclosed in PCT/EP03/09151, further processing may include the step of engaging with the clamp part a cover part engageable with the clamp part and/or the vial to cover the region of the upper surface of the closure part which is exposed through the aperture when the clamp part is engaged with the vial.

In step (3) the construction, operation and layout of the source of the beam of electrons is an important feature of this invention.

It is desirable to ensure that as high a proportion as possible of any micro-organisms (the term as used herein refers to any type of micro-pathogen, including bacteria, viruses, spores etc.) contaminating at least the wall part to be punctured by the needle, preferably the entire outer surface of the container, are inactivated prior to puncturing the containers. Preferably at least a 3 log reduction of any viable micro-organisms is achieved, preferably at least a 6 log reduction. This is usually measured by monitoring the reduction of activity of *B. pumilus*, a micro-organism having one of the highest resistance to electron beam radiation. For a particular application standards of reduction may be set by regional authorities such as the US FDA or corresponding European bodies, such as Sterility Assurance Levels.

To achieve this degree of inactivation it is believed that the means for exposing the wall part of the container to a beam of electrons should generate an electron beam which has an energy of at least 50 KeV as it strikes the outer surface of the wall part, e.g. 50-85 KeV. It is believed to be preferable for electrons of the beam to penetrate 0.1 mm depth into the surface of the wall part, e.g. an elastomeric vial closure, to achieve such reduction of activity, and that this energy is suitable to result in such penetration without also resulting in the electrons passing through the wall part e.g. through a vial closure into the interior of the container. It is also believed that to achieve suitable reduction of micro-organism activity a dose of at least 25 K Gray (KGy) of electron beam energy is desirable over the region of the wall part which is to be punctured by the needle. The total electron beam current to achieve suitable reduction of activity is preferably in the range 1-3 mA, e.g. 2-2.5 mA.

To achieve this an advantageous type of electron beam generator is provided. Such a generator, a process as described above using such a generator in step (3), and an apparatus as described above comprising such a generator as a means for exposing the wall part to a beam of electrons of a sufficient energy and dose to inactivate microorganisms present on the wall part in step (3), comprise further aspects of this invention.

Electron beams are normally generated by means of a so called "electron gun". Typically such a gun comprises a vacuum chamber enclosing a cathode, such as a heated tungsten filament, and an anode spaced apart from the cathode and which comprises or is adjacent to a window in a wall part of the chamber, means to apply a potential difference between the cathode and anode, so that electrons are emitted from the cathode, accelerate across the vacuum toward the anode, and by the time the electrons reach the vicinity of the anode they have such a high energy that they travel at high speed past or through the anode, and travel through the window to emerge as an electron beam.

In the gun of the invention it is preferred to apply a sufficient potential difference between the cathode and anode that the electrons are accelerated to an energy of ca. 75-85 KeV, e.g. ca. 80 KeV, then to allow these electrons to pass through a metal chamber wall of the vacuum chamber, e.g. a titanium wall, typically ca. 4 to 8 microns thick such that the electrons reaching the wall part of the container in step (3) have an energy ca. 50 KeV. Such a thin wall may be supported, e.g. against external atmospheric pressure, by a supporting grid. It is found that if the wall part of the containers, e.g. the outer surface of the vial closure, passes within ca. 25 mm, preferably 10-15 mm, of the chamber wall of such an electron beam generator, electrons accelerated to an energy of ca. 75-85 KeV have sufficient energy that passage through the air gap between the window and the container still leaves them with sufficient energy, e.g. ca. 50 KeV, to achieve the desired reduction of micro-organism activity after crossing this air gap. The generator is preferably mounted relative to the conveyor such that the electrons travel downwards toward the upward facing wall part of the container.

Suitably therefore the means for exposing the wall part of the container to a beam of electrons is configured to deliver electrons having an energy of at least 50 KeV, and a dose of at least 25 K Gray (KGy) of electron beam energy over the region of the wall part which is to punctured by the needle during step (3).

It will be appreciated that the impact of energetic electrons with oxygen atoms in the air will generate ozone, so it is desirable that the enclosure is provided with extraction equipment to remove this ozone.

In a preferred construction the electron beam generator comprises plural cathodes arranged in an array, suitably a substantially horizontal planar array, adjacent to, suitably above, the conveyor, such that electron beam emission from cathodes of the array overlap in a region of overlap, and the container e.g. a vial is transported relative to the array such that the wall part of the container, e.g. the part of a vial closure which is to be punctured passes through at least one region of overlap. In the region of overlap the electrons should have the above-mentioned energy, i.e. of at least 50 KeV as the beam strikes the outer surface of the wall part, e.g. 50-85 KeV, and so that a dose of at least 25 K Gray (KGy) of electron beam energy is delivered over the region of the wall part which is to punctured by the needle. An advantage of arranging cathodes in this way is that the intensity of electron beam emission from each cathode decreases with distance according to well known laws, and the overlap causes a summation of electron beam emission tending to reduce this decrease.

Preferably in this array at least one group of three cathodes is arranged in a triangle with a cathode at each apex of the triangle, so that the electron emission of the three cathodes overlaps about the centre of the triangle. It is found in this arrangement, with the construction of electron beam source disclosed herein, that a minimum of four cathodes arranged in a quadrilateral array, e.g. in a regular parallelogram array, with a cathode at each corner, is suitable to achieve plural regions of overlap, and is suitable to achieve a sufficient degree of reduction of microorganism activity on the surface exposed to the electron beam. Preferably six, or more preferably eight, cathodes are arranged such that any four of the cathodes are in such a regular parallelogram array. Eight cathodes arranged in this way can create six regions of overlap in which the electron emission of three cathodes overlaps.

For example in such an array, relative to the longitudinal direction in plan of a conveyor transporting containers arranged serially along the conveying direction, cathodes, e.g. four cathodes, may be arranged in a row along the longitudinal direction on one side of the centre of the conveyor, preferably equally longitudinally spaced, and cathodes, e.g. four cathodes, may be arranged in a row along the longitudinal direction on the opposite side of the centre of the conveyor, preferably also equally longitudinally spaced, cathodes on one side of the centre of the conveyor being longitudinally displaced relative to cathodes on the opposite sides.

Alternatively in the array there may be a single row of cathodes arranged sequentially longitudinally parallel to the line of the conveyor, spaced so that the electron emission of longitudinally adjacent cathodes overlaps. It is found that with the construction of electron beam source disclosed herein, six to eight cathodes, for example seven cathodes, is suitable to achieve a sufficient degree of reduction of micro-organism activity on the surface exposed to the electron beam.

Preferably the array is arranged so that the regions of overlap are aligned linearly along the longitudinal centre line of the conveying direction of the conveyor. Preferably each region of overlap is at least as large as the wall part of the container, or in the case of a container being a vial, as large as the closure of a vial. In the case of the vials of PCT/EP03/09151 as large as the upper surface of the clamp part.

A suitable current I in mA to achieve a suitable reduction of micro-organism activity at the surface of the closure of a vial can be calculated from the equation:

$$\frac{I(\text{mA})}{\text{width (cm)}} = \frac{\text{dose } (Kgy) \times v(\text{cm/s})}{1000 \times SP(Mev.\text{cm}^2/g)}$$

where the stopping power (SP) for an energy of 50 KeV is 6.5 MeV·cm²/g, width is the width of the vial closure, v is the velocity in cm/sec of the vial closure. On this basis for vial closures with a diameter of 2.225 cm and a throughput of 12 vials/sec, typically 36 cm/sec, the current on the closures is 0.138 mA/cm. For a width of window across the longitudinal direction of the conveyor a suitable electron beam current is 0.83 mA.

Suitably the means for exposing the wall part of the container to a beam of electrons comprises a tunnel enclosing one or more electron beam generator as described above, through which the containers, e.g. vials, are conveyed. Such a tunnel is suitably located within the enclosure.

Suitable constructions of such an electron beam generator will be apparent to those skilled in the art.

The invention will now be described by way of example only with reference to the accompanying figures.

Figure 1:
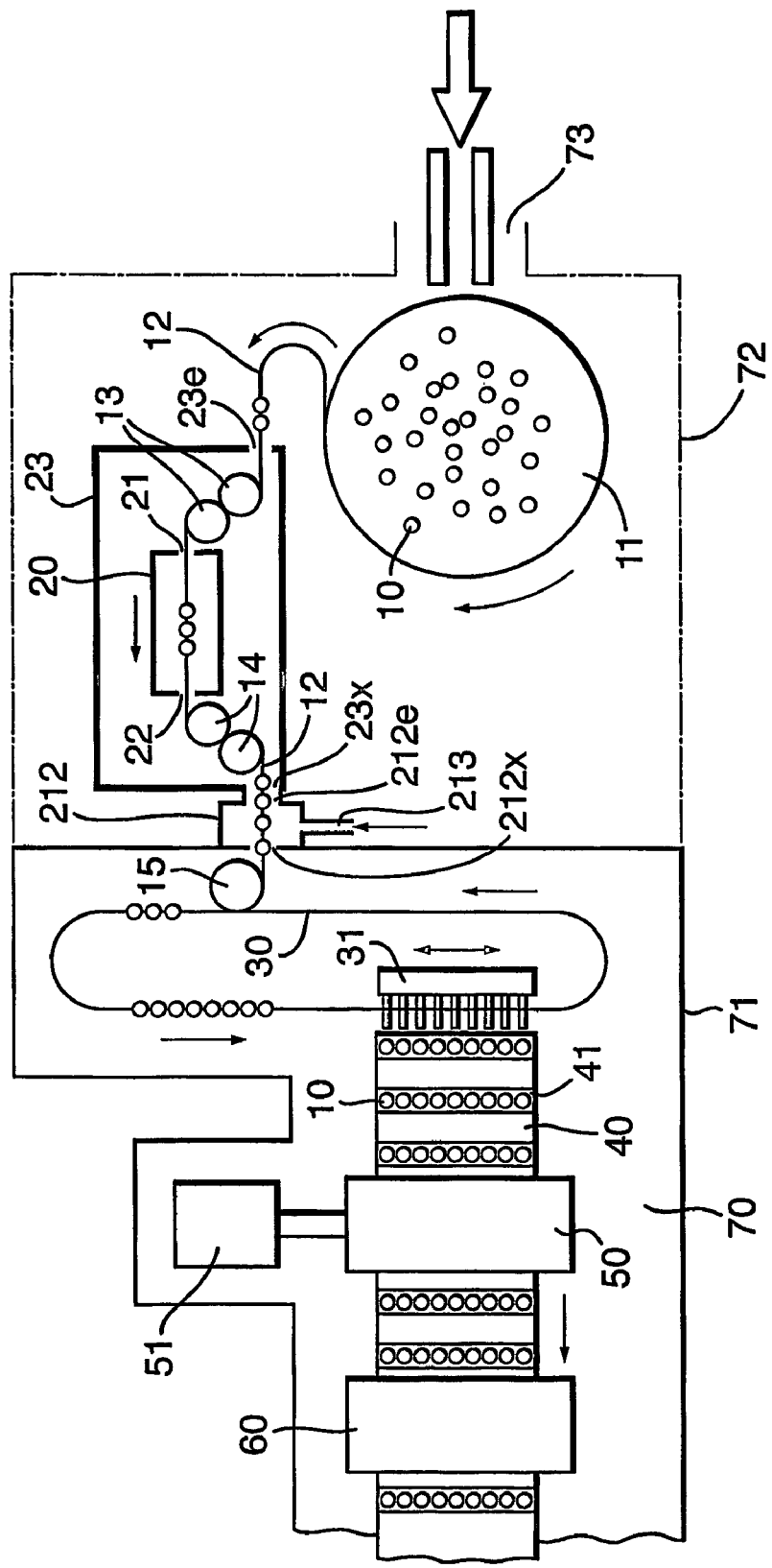
FIG. 1 shows in plan the overall layout of an apparatus for performing the process of this invention.
Figure 3:
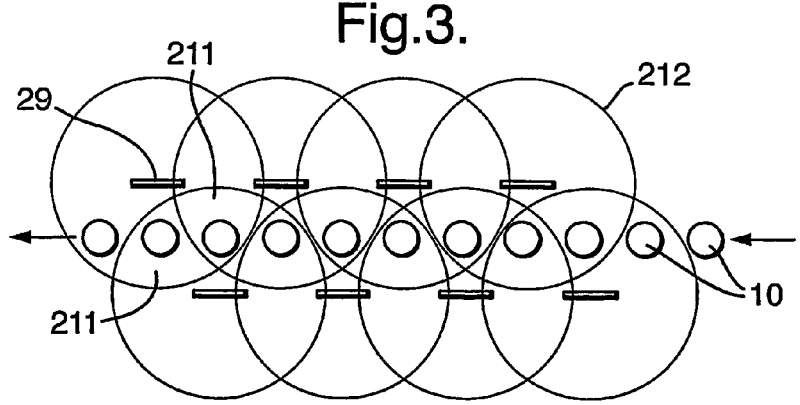

FIG. 3 a schematic plan view of an arrangement of cathodes relative to vials in the electron beam tunnel of the apparatus of FIG. 1.

Figure 4:
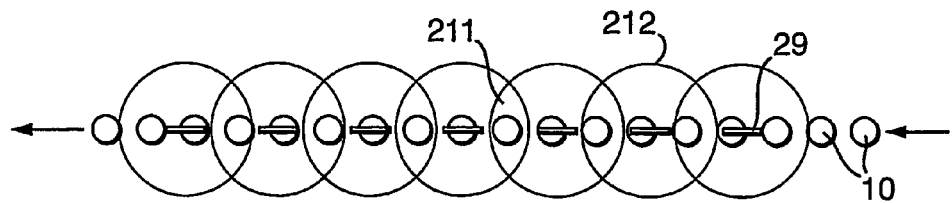

FIG. 4 a schematic plan view of an alternative arrangement of cathodes relative to vials in the electron beam tunnel of the apparatus of FIG. 1.

FIG. 5 a longitudinal section of a vial and closure suitable for use in the process of this invention.

Referring to FIG. 1, vials 10 shown schematically in plan, are loaded manually onto a conventional rotating loading table 11.

Figure 2:
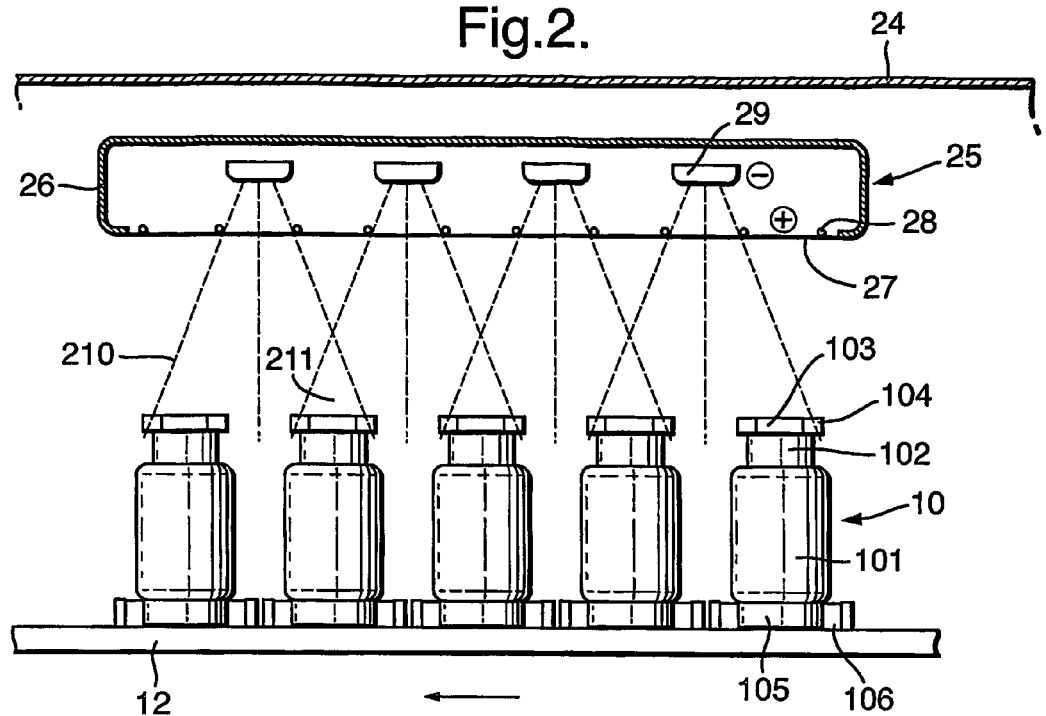
FIG. 2 shows a longitudinal section through the electron beam tunnel of the apparatus of FIG. 1.

FIG. 2 shows the construction of the vials 10 more clearly. Each vial 10 consists of a hard plastic body 101 with an upper neck 102 having an upper mouth opening (not shown) which is closed by a thermoplastic elastomer closure 103, which is held in place on the neck 102 in a closing relationship with the mouth by means of clip 104. This construction is generally conventional in the art. A particular construction of vial, being that disclosed in PCT/EP03/09151 is shown in FIG. 5. The interior of the vials 10 has been previously sterilised e.g. by gamma radiation.

From loading table 11 the vials 10 are taken up by a first conveyor 12 in a conventional manner, the vials 10 being held on the conveyor 12 by their base 105. To assist this, as shown in FIG. 2 the vials 10 are mounted in small mountings 106. Such mountings 106 may comprise ring-shaped plastic material mountings into which the base 105 of a vial 10 may fit by a friction or snap-fit. Only a few representative vials 10 are shown at various points on conveyor 12.

The conveyor 12 transports the vials 10 through a shielded tunnel 20 in which the vials are exposed to electron beam radiation. The walls of the tunnel 20 are shielded by surrounding lead blocks forming an enclosing wall of an enclosure 23. The conveyor 12 introduces the vials 10 into the tunnel serially in line with the conveying direction, in through an entrance opening 21 of the electron beam tunnel 20 and out through an exit opening 22 of the electron beam tunnel 20. The path of the conveyor 12 bends shortly before the entrance opening 21 of the tunnel 20 and shortly after the exit opening 22 of the tunnel 20, so that shielding 23 can be positioned in front of these openings 21,22, to obstruct any straight line path from the electron beam source through openings 21,22. Star wheel systems 13, 14 facilitate this change in direction of motion of the vials 10.

Enclosure 23, which is bounded by the surrounding wall of lead blocks, has an entrance opening 23e via which vials 10 may enter the enclosure 23 by means of conveyor 12, and an exit opening 23x via which vials 10 may exit the enclosure 23, and within which is located the electron beam tunnel 20. The lead block shielding of this enclosure prevents electron beam radiation and X-ray radiation caused by the electron beam from escaping from the enclosure 23 at an intensity likely to cause damage or injury. It is seen that the enclosure 23 is quite compact, and therefore minimises the amount of heavy shielding required. The electron beam tunnel 20 may conveniently be mounted on a removeable roof of enclosure 23 to facilitate access thereto for maintenance etc.

FIGS. 2, 3 and 4 show in more detail the construction and layout of the electron beam tunnel 20. The tunnel 20 has a shielded roof 24, beneath which is mounted an electron beam generator 25. The electron beam generator 25 comprises a vacuum chamber bounded by a wall 26. Part 27 of the wall 26 comprises a window of four micron thick titanium, supported by a wire grid 28. This window 27 is positively charged and forms an anode. Within the vacuum chamber 25 are mounted cathodes 29 being tungsten filaments which can be electrically heated and from which electrons are emitted, cathodes 29 being electrically isolated across the vacuum within chamber 25 from anode 27. These electrons accelerate across the vacuum chamber 25 toward the anode 27, and by the time the electrons reach the vicinity of the anode 27 they have such a high energy that they travel at high speed through the window 27 to emerge as an electron beam 210. The electron beam generator 25 is set up in a conventional manner such that the electron beam 210 has an energy of ca. 50 KeV as it emerges from the window 27.

As can be seen more clearly in FIG. 3, eight cathodes 29 are arranged in a horizontal array above the conveyor. In this array, any three cathodes 29 are arranged at the apexes of a triangle. The eight cathodes 29 are arranged in an array which comprises four cathodes 29 arranged equally longitudinally spaced in a row along the longitudinal direction on one side of the centre of the conveyor 12, and four cathodes 29" arranged equally longitudinally spaced in a row along the longitudinal direction on the opposite side of the centre of the conveyor 12.

As can be seen more clearly in FIG. 4, seven cathodes 29 are arranged in a horizontal array above the conveyor. In this array the cathodes 29 are arranged in a single linear row of cathodes 29 arranged sequentially longitudinally parallel to the line of the conveyor 12 beneath them, and spaced so that the electron emission of longitudinally adjacent cathodes 29 overlaps.

As seen in FIGS. 2, 3 and 4 this causes the electron beam emission from the cathodes to overlap in regions 211. As seen in FIG. 3 at regions 211 about the centre of the triangles formed by three cathodes 29 the emission from three cathodes overlaps. In FIG. 3 circles 212 centred on respective cathodes 29 link points of equal electron beam emission intensity from cathodes 29 at the centre of these circles 212. As seen in FIG. 4 at regions 211 between longitudinally adjacent pairs of cathodes 29 the emission from two cathodes overlaps. In FIG. 4 circles 212 centred on respective cathodes 29 link points of equal electron beam emission intensity from cathodes 29 at the centre of these circles 212. Therefore electron beam intensity is maximised in these regions of overlap 211. In these regions of overlap 211, at the distance at which the vial closure is transported beneath the window 27 the electron beam energy is at least 50 KeV.

It is found that for a conveying speed of vials of ca. 12 vials per second, e.g. 36 cm/sec, a window 27 with an area 250 mm×60 mm is suitable, with an array of cathodes 29 as shown in FIG. 3 occupying a generally corresponding area.

The conveyor 12 transports the vials 10 along the conveying direction indicated by the arrow in FIG. 3 such that the upper outer surface of the closures 103 pass ca. 15 mm below the lower outer surface of window 27. The vial closures 103 therefore pass through plural regions 211 of electron beam emission overlap. It is seen that at the distance at which the vial closures 103 are transported below the window 27 the region of overlap 211 has a greater area than the upper surface area of the closure 103. When the vial with its closure is of the type disclosed in PCT/EP03/09151 or as shown in FIG. 5 the electron beam should impinge upon at least the whole area of the part 84A of the closure 80. The electron beam generator 25 is set up such that the electron beam 210 dosage received by the upper outer surface of a closure 103 on passing through all of the regions of overlap 211 is sufficient to inactivate any micro-organism contamination present on the upper outer surface to a suitable extent, e.g. 6 logs reduction, e.g. determined as described above.

The tunnel 20 is provided with a means, e.g. an extraction pump (not shown) to remove ozone generated in tunnel 20 by the effect of the electron beam on atmospheric oxygen.

On leaving the exit opening 22 of the electron beam tunnel 20 the conveyor 12 transports the vials 10 within the enclosure 23 toward the exit opening 23x of enclosure 23, the direction of conveying motion being bent as the vials 10 are conveyed by star wheels 14.

On passing through exit opening 23x and out of enclosure 23 the vials 10 are conveyed into the compartment 212. This compartment 212 is provided with a means to introduce pressurised (60 Pascals) sterile air (Class 100) into the compartment 212, being the inlet conduit 213. The compartment 212 is otherwise closed except for its entrance 212e through which vials 10 are conveyed into the compartment 212, and exit 212x through which vials 10 are conveyed out of the compartment 212. The entrance 212e is in communion with the exit opening 23x of the enclosure 23, and the entrance 212e is larger than the exit 212x so that the pressurised air preferentially leaves the compartment via the entrance 212e. This directs a flow of the sterile air in a direction opposite to the conveying direction and can reduce the possibility of contamination being carried downstream into the areas where steps (5) and (6) are subsequently performed (see later). The flow of pressurised air flows in the upstream direction of the conveyor 12 into enclosure 23 and helps to flush ozone resulting from the electron beam, out of the enclosure 23.

Conveyor 12 then conveys the vials 10 to a second, intermediate, conveyor 30. Vials are transferred from conveyor 12 onto the conveyor 30 by a conventional means such as a star wheel 15, whilst conveyor 12 follows a return track (not shown). On conveyor 30 the vials 10, still held adjacent to their base, are aligned in a serial line parallel to the conveying direction of conveyor 30. Vials 10 are now transferred from intermediate conveyor 30 onto third conveyor 40, on which the vials 10 are transported to filling station 50 and sealing station 60. On conveyor 40 the vials 10, still held adjacent to their base 105, are aligned in rows across the conveying direction of conveyor 40.

To change the alignment of the rows of vials 10 relative to the conveying direction, conveyor 30 transports vials 10 to an floating pulley 31 of generally conventional construction and operation. Floating pulley 31 moves relative to conveyor 30 so as to have zero relative velocity relative to conveyor 30 in the conveying direction indicated by the arrow and removes vials 10 from conveyor 30. Floating pulley 31 then stops so as to have zero relative velocity transverse to the conveying direction (indicated by the arrow) of third conveyor 40. Then floating pulley 31 transfers vials 10 onto conveyor 40, which receives the vials 10 on holders 41 in plural rows arranged across the conveying direction of conveyor 40. Alternatively for example a pick-and-place robot system may be used to transfer vials 10 from conveyor 30 onto conveyor 40.

Conveyor 40 then transports the vials 10 to filling station 50 at which liquid medicament is then introduced into the vials 10. Filling station 50 comprises known means for puncturing the vial 10 with a filling needle, introducing the medicament into the vial 10 via the needle then withdrawing the needle. Such means are arranged in plural across the conveying direction of conveyor 40 so as to fill plural vials 10 in this manner simultaneously. Filling station 50 may also comprise ancillary equipment 51 by which the medicament may be fed to filling station 50 and replenished when necessary. Filing station 50 preferably incorporates means (not shown) by which vials 10 on the conveyor may be held down on the conveyor by means of the stand 106, against the withdrawing force as the needle is withdrawn. Conveyor 40 then conveys the filled vials 10 to sealing station 60 where the residual puncture site in closure 103 left by the filling needle at filling station 50 is sealed by melting the material adjacent to the puncture site, using a laser beam directed at the residual puncture site, and then allowing the material to re-solidify.

The filling station 50 and sealing station 60 and the conveyors 30, 40 are maintained under a downward flow of purified air of class 100 or better. By holding the vials 10 on the respective conveyors 12, 30, 40 by their base, with the closure uppermost, it is thereby ensured that the part of the closure 103 which has been exposed to the electron beam 210 is maintained in a part of this flow of air which is upstream of any part of the vial 10 which has not been exposed to the electron beam 210. Preferably the entire conveyor system including the table 11 and the sealing station 60 is maintained in this downward flow of purified air.

Ways of providing such a flow of purified air will be apparent to those skilled in the art. As shown conveyor 12 transports the vials 10 through an entrance opening of an enclosure 70 defined by rigid vertical barriers 71, and within which a downward laminar flow of purified air is maintained, having a purity of Class 100 or better. This air may be the same air fed into the compartment 24. The enclosure 70 may include glove ports, air locks etc. not shown by means of which operatives can access the parts of the apparatus within the enclosure 70 without introducing contamination. For example in particular such an air lock or glove port etc. (not shown) may be positioned adjacent to ancillary equipment 51 to enable this equipment to be loaded or otherwise maintained. The exit 27 of compartment 26 is in communion with a corresponding opening through barrier 71.

A downward laminar flow of air is also maintained in area 72 into which an operator may manually load vials 10 onto the rotating loading table 11 using vial loading system 73. Area 72 may also optionally be enclosed by rigid vertical partitions, and the downward laminar flow of air within area 72 may be such as to generate an air curtain preventing the ingress of contamination into the area 72.

Downstream of sealing station 60 the vials 10 may be for example subjected to further processing, such as capping, secondary packaging etc. at respective capping, secondary packaging stations etc., before being removed from the conveyor 40. When vials 10 of the type disclosed in PCT/EP03/09151 e.g. as shown in FIG. 5 are used such further processing may include the fitting of a cover part over the clamp part.

At various points along the conveyors 12, 30, 40 the vials may be monitored e.g. to check their weight, to check that a suitable weight of medicament has been introduced at the filling station 50, etc.

Referring to FIG. 5, a longitudinal (up-down) sectional view of a vial 10 suited to the apparatus and process of this invention is shown, being that of PCT/EP03/09151, and showing in more detail the vial 10 shown in FIG. 2. The vial 10 is of generally cylindrical shape with a mouth opening 81 at its upper end, and with a neck 82 (corresponding to neck 102 in FIG. 2) immediately below. Mouth opening 81 is surrounded by an outwardly extending rim 83 having an upper surface 83A and a lower surface 83B, the upper surface 83A being bounded by a peripheral kerb 84, and a sealing ridge 85 extending upwardly. Inserted into mouth opening 81 and extending some way down neck 82 is a plug part 86 of a closure part 87 (corresponding to closure 103 of FIG. 2) made integrally of a thermoplastic elastomer material and being a tight fit into the neck 82 to thereby form a tight seal between the closure part 87 and neck 82. The closure part 87 has an outwardly extending flange 88, of shape and dimensions to fit comfortably within kerb 84, with the sealing ridge 85 compressing and deforming the elastomer material, contributing to a good seal between surface 83A and closure 87. A clamp part 89 (corresponding to clip 104 of FIG. 2) holds the closure part 87 in place against the flange 83. The clamp part 89 comprises a skirt wall 810 having a snap fit engagement part 811 which can engage under flange 83 to hold the clamp part 89 in place on the assembly of vial 10 and closure part 87. In the upper wall of the clamp part 89 is a central circular aperture 812, through which bulges the central convex part of the upper part of closure part 87 so that a central region 813 of the upper wall of the closure part 87 is exposed through the aperture 812. Around the periphery of the clamp part 88 is a groove 814 with which a corresponding bead of a cover part (not shown)

can snap-fit engage. The base 815 of the vial 10 is mounted in a ring-shaped stand 816 with which base 815 engages in a tight friction or snap fit.

The invention claimed is:

1. An apparatus for introducing a medicament into a container having a wall part which is puncturable and which can be thermoplastically melted, characterised by:
    an enclosure which encloses means for exposing the wall part of the container to a beam of electrons of a sufficient energy and dose to inactivate microorganisms present on the wall part of the container,
    means to transport a container into said enclosure,
    means to transport the container out of said enclosure,
    a filling station situated outside of the enclosure and comprising means for puncturing the wall part with a filling needle, introducing the medicament into the container via the needle then withdrawing the needle,
    means for transporting a container which has been exposed to said beam of electrons from the enclosure to the filling station,
    means for providing a sterile environment around the container whilst the container is transported from the enclosure to the filling station.

2. Apparatus according to claim 1 characterised by additionally including a sealing station at which the residual puncture site is sealed by melting the material adjacent to the puncture site and then allowing the material to re-solidify.

3. Apparatus according to claim 1 characterised in that the enclosure is bounded by a surrounding wall, having an entrance opening via which a container may enter the enclosure, and an exit opening via which a container may exit the enclosure, and within which is located a source of a beam of electrons.

4. Apparatus according to claim 1 characterised in that the enclosure is a shielded enclosure.

5. Apparatus according to claim 1 characterised by a conveyor to introduce plural conveyors into the enclosure serially in line with the conveying direction.

6. Apparatus according to claim 5 wherein the conveyor follows a convoluted path within the enclosure.

7. Apparatus according to claim 1 characterised by a compartment located downstream in the conveying direction from the enclosure, provided with a means to introduce a pressurised sterile atmosphere into the compartment, having an entrance for the container, the entrance being in communion with the exit opening of the enclosure, and having an exit for the container, and the conveyor pass through the compartment from the entrance to the exit.

8. Apparatus according to claim 7 characterised in that the entrance of the compartment is larger than the exit so that the pressurised atmosphere preferentially leaves the compartment via the entrance.

9. Apparatus according to claim 1, characterised by a conveyor which conveys containers through the enclosure in a serial line, and by means between the enclosure used in step (2) and the filling station of step (4) to convert such serial movement of plural vials in line with the conveying direction into movement in the conveying direction of rows of plural vials aligned across the conveying direction.

10. Apparatus according to claim 1 characterised in that the means for exposing the wall part of the container to a beam of electrons comprises a vacuum chamber enclosing a cathode and an anode spaced apart from the cathode and which comprises or is adjacent to a window of a wall part of the chamber, means to apply a potential difference between the cathode and anode, so that electrons are emitted from the cathode, accelerate across the vacuum toward the anode, and travel through the window to emerge as an electron beam.

11. Apparatus according to claim 1 characterised in that the means for exposing the wall part of the container to a beam of electrons generates an electron beam current in the range 1-3 mA.

12. Apparatus according to claim 10 characterised in that the means for exposing the wall part of the container to a beam of electrons and is configured to apply a sufficient potential difference between the cathode and anode that the electrons are accelerated to an energy of ca. 75-85 KeV.

13. Apparatus according to claim 12 characterised in that the wall part of the container is arranged to pass within 25 mm of the chamber wall of the electron beam generator.

14. Apparatus according to claim 10 characterised in that in the means for exposing the wall part of the container to a beam of electrons is configured to deliver electrons having an energy of at least 50 KeV, and a dose of at least 25 K Gray (KGy) of electron beam energy over the region of the wall part which is to be punctured by the needle.

15. Apparatus according to claim 10 characterised by plural cathodes arranged in an array adjacent to the conveyor, such that electron beam emission from cathodes of the array overlap in a region of overlap, and the container is conveyed relative to the array such that the wall part of the container, which is to be punctured passes through at least one region of overlap.

16. Apparatus according to claim 15 characterised by an array in which at least one group of three cathodes is arranged in a triangle with a cathode at each apex of the triangle, so that the electron emission of the three cathodes overlaps about the centre of the triangle.

17. Apparatus according to claim 16 characterised by at least four cathodes arranged in a quadrilateral array with a cathode at each corner.

18. Apparatus according to claim 17 characterised by eight cathodes arranged to create six regions of overlap in which the electron emission of three cathodes overlaps.

19. Apparatus according to claim 15 characterised in that relative to the longitudinal direction in plan of a conveyor transporting containers arranged serially along the conveying direction, cathodes are arranged in a row along the longitudinal direction on one side of the centre of the conveyor and cathodes are arranged in a row along the longitudinal direction on the opposite side of the centre of the conveyor, cathodes on one side of the centre of the conveyor being longitudinally displaced relative to cathodes on the opposite sides.

20. Apparatus according to claim 15 characterised by an array of single row of cathodes arranged sequentially longitudinally parallel to the line of the conveyor, spaced so that the electron emission of longitudinally adjacent cathodes overlaps.

21. Apparatus according to claim 20 characterised by six to eight cathodes.

22. Apparatus according to claim 15 characterised in that the array is arranged so that the regions of overlap are aligned linearly along the longitudinal centre line of the conveying direction of the conveyor.

23. Apparatus according to claim 1 characterised in that the means for exposing the wall part of the container to a beam of electrons comprises a tunnel enclosing one or more electron beam generator through which the container is conveyed.

24. A process for introducing a medicament into a container characterised by the steps:
(1) providing a container having a wall part of a material which can be punctured by a filling needle and thermoplastically melted,
(2) introducing the container into an enclosure which encloses a means for exposing the wall part of the container to a beam of electrons of a sufficient energy and dose to inactivate microorganisms present on the wall part of the container,
(3) exposing the wall part to a beam of electrons of a sufficient energy and dose to inactivate microorganisms present on the wall part, whilst the container is in said enclosure,
(4) transporting exposed containers from (3) out of the enclosure, and transporting them in a sterile environment to a filling station,
(5) at the filling station puncturing the wall part with a filling needle, introducing the medicament into the container via the needle, and withdrawing the needle.

25. Process according to claim 24 characterised in that step (5) is followed by a step (6) transporting filled containers from step (5) to a sealing station where the residual puncture site is sealed by melting the material adjacent to the puncture site and then allowing the material to re-solidify.

* * * * *